US008317724B2

(12) United States Patent
Taylor et al.

(10) Patent No.: US 8,317,724 B2
(45) Date of Patent: Nov. 27, 2012

(54) TARGETED TREATMENT DELIVERY SYSTEM

(75) Inventors: James D. Taylor, Bridgeton, MO (US); Bruce Olson, St. Louis, MO (US); Stephen Lewis, Florissant, MO (US)

(73) Assignee: Envisioneering, LLC, St. Louis, MO (US)

( * ) Notice: Subject to any disclaimer, the term of this patent is extended or adjusted under 35 U.S.C. 154(b) by 30 days.

(21) Appl. No.: 12/968,870

(22) Filed: Dec. 15, 2010

(65) Prior Publication Data

US 2011/0144492 A1 Jun. 16, 2011

Related U.S. Application Data

(60) Continuation of application No. 12/214,163, filed on Jun. 17, 2008, now abandoned, which is a division of application No. 11/895,228, filed on Aug. 23, 2007, now Pat. No. 7,833,168, which is a continuation of application No. 10/842,652, filed on May 10, 2004, now abandoned.

(60) Provisional application No. 60/494,910, filed on Aug. 13, 2003.

(51) Int. Cl.
*A61B 10/00* (2006.01)

(52) U.S. Cl. ....................................... 600/562

(58) Field of Classification Search ........... 600/562–572
See application file for complete search history.

(56) References Cited

U.S. PATENT DOCUMENTS

| 5,149,598 A | 9/1992 | Sunshine |
|---|---|---|
| 5,398,690 A | 3/1995 | Batten et al. |
| 5,456,258 A | 10/1995 | Kondo et al. |
| 5,660,185 A | 8/1997 | Shmulewitz et al. |
| 5,833,627 A | 11/1998 | Shmulewitz et al. |
| 5,843,050 A | 12/1998 | Jones et al. |
| 5,873,828 A | 2/1999 | Fujio et al. |
| 5,885,258 A | 3/1999 | Sachdeva et al. |
| 6,102,867 A | 8/2000 | Dieta et al. |
| 6,149,598 A | 11/2000 | Tanaka |
| 6,171,249 B1 | 1/2001 | Chin |
| 6,179,249 B1 | 1/2001 | Canadas |
| 6,238,336 B1 | 5/2001 | Ouchi |
| 6,261,234 B1 | 7/2001 | Lin |
| 6,261,243 B1 | 7/2001 | Burney |
| 6,334,067 B1 | 12/2001 | Brabrand |
| 6,390,973 B1 | 5/2002 | Ouchi |
| 6,409,666 B1 | 6/2002 | Ito |
| 6,419,641 B1 | 7/2002 | Mark et al. |
| 6,443,909 B1 | 9/2002 | Ouichi |
| 6,447,477 B2 | 9/2002 | Burney et al. |

(Continued)

OTHER PUBLICATIONS

"Execution of Robot-Assisted Biopsies Within The Clinical Context," Rovetta et al, Journal of Image Guided Surgery, 1: 280-287, 1995.

(Continued)

*Primary Examiner* — Jeffrey G Hoekstra
(74) *Attorney, Agent, or Firm* — Gordon & Jacobson, PC (57) ABSTRACT

This invention relates generally to the targeting and biopsy of tissue for medical purposes, and more particularly to a targeted biopsy system which allows planning of tissue to be sampled, targeting of specific areas of tissue in reference to the plan, capturing the tissue sample and recording the source location of the tissue sample, particularly for use in collecting tissue samples from the prostate gland. A further purpose of this invention is to provide a targeted treatment system which allows planning of tissue to be treated, targeting of specific areas of tissue in reference to the plan, and delivering the treatment to the targeted tissue.

34 Claims, 11 Drawing Sheets

U.S. PATENT DOCUMENTS

| | | |
|---|---|---|
| 6,485,411 B1 | 11/2002 | Konstorum et al. |
| 6,591,130 B2 | 7/2003 | Shahidi |
| 6,685,648 B2 | 2/2004 | Flaherty et al. |
| 6,689,067 B2 | 2/2004 | Sauer et al. |
| 6,749,560 B1 | 6/2004 | Konstorum et al. |
| 6,884,219 B1 | 4/2005 | Pruter |
| 7,033,374 B2 | 4/2006 | Schaefer et al. |
| 7,171,255 B2 | 1/2007 | Holupka et al. |
| 2002/0002349 A1 | 1/2002 | Flaherty et al. |
| 2002/0082518 A1 | 6/2002 | Weiss et al. |
| 2002/0111634 A1 | 8/2002 | Stoianovici et al. |
| 2002/0123689 A1 | 9/2002 | Furai |
| 2002/0143291 A1 | 10/2002 | Slater |
| 2003/0050574 A1 | 3/2003 | Krueger |
| 2003/0078502 A1 | 4/2003 | Miyaki et al. |
| 2003/0120154 A1 | 6/2003 | Sauer et al. |
| 2003/0135119 A1 | 7/2003 | Lee et al. |
| 2003/0195432 A1 | 10/2003 | Kortenbach et al. |
| 2004/0030250 A1 | 2/2004 | Stewart |
| 2004/0054377 A1 | 3/2004 | Foster et al. |
| 2004/0133111 A1 | 7/2004 | Szczech et al. |
| 2005/0203413 A1 | 9/2005 | Fichtinger et al. |
| 2007/0293787 A1 | 12/2007 | Taylor et al. |
| 2009/0054807 A1 | 2/2009 | Taylor et al. |

OTHER PUBLICATIONS

"Transrectal Prostate Biopsy Inside Closed MRI Scanner with Remote Actuation, under Real-Time Image Guidance," Fichtinger et al, MICCAAI 2002, LNCS 2488 pp. 91-98, 2002.

"A Robotic System for Transrectal Needle Insertion into the Prostate with Integrated Ultrasound", Chad M. Schneider et al., Proceedings of the 2004 IEEE International conference on Robotics & Automation, Apr. 2004, pp. 365-370.

U.S. Appl. No. 60/493,406, filed Aug. 7, 2003, Fichtinger et al.

TARGETED TREATMENT DELIVERY SYSTEM

CROSS REFERENCE TO RELATED APPLICATION

This application is a continuation of patent application Ser. No. 12/214,163, which was filed on Jun. 17, 2008, now abandoned, and which is a divisional patent application that claims priority to the non provisional patent application having Ser. No. 11/895,228, which was filed on Aug. 23, 2007, now issued as U.S. Pat. No. 7,833,168, which is a continuation of the nonprovisional patent application having Ser. No. 10/842,652 that was filed on May 10, 2004, now abandoned, which claims priority to the provisional patent application having Ser. No. 60/494,910, filed Aug. 13, 2003. All four of such prior applications are hereby incorporated herein by reference in their entireties.

BACKGROUND OF THE INVENTION

Prostate health is a significant concern for men over the age of fifty. If prostate cancer is suspected from either a physical examination or because of a Prostate Specific Antigens test, a biopsy is performed to collect tissue samples from the prostate for evaluation by a pathologist. Prostate tumors are small growths scattered about the prostate. For this reason, a physician will take multiple tissue samples from different areas of the prostate, typically between 9 and 18 samples.

The normal procedure for obtaining biopsy samples with ultrasound guidance is called Transrectal Ultrasound (TRUS) Guided Prostate Biopsy. An end-fire ultrasound probe is used, which generates a pie-shaped image plane. Some end-fire probes are manufactured with a biopsy needle channel, which passes through the body of the probe at an angle, such that a biopsy needle set inserted through the biopsy needle channel exits the channel at a slight angle relative to the body of the probe. Most probes require a needle set guide tube to be affixed to the probe body, such that a needle set placed through the guide tube parallels the axis of the probe and the needle set can be extended beyond the end of the probe. In use for both, the physician inserts the ultrasound probe into the rectum, and moves the probe around until the specific area of the prostate to be sampled is identified. The physician then bends the probe upward, pointing the biopsy needle channel or biopsy needle set guide at the targeted area of the prostate. A needle set is inserted into and through the needle channel or guide, pushed through the rectum wall and into the prostate.

Standard coring biopsy needles sets are made from substantially rigid, coaxially aligned, stainless steel wire and tubing. They are comprised of two basic components; an inner solid wire stylet with specimen notch and a hollow outer cutting cannula. Once the needle set is correctly positioned relative to the area of tissue to be sampled, the inner stylet is quickly advanced under spring loaded or similar pressure into the prostate tissue. The tissue to be sampled then "prolapses" into stylet's sample notch cutout. Almost instantaneously the outer cutting cannula quickly advances, also under spring loaded pressure, which serves to sever and capture the tissue that had prolapsed into the stylet notch. The needle set is then removed from the tissue/patient so that the tissue sample can be extracted from the needle set and evaluated for the presence of cancer. The physician then moves the probe around within the rectum to identify the next area of the prostate to be sampled, and the process is repeated. As noted, between 9 and 18 samples are typically taken from different areas of the prostate.

Existing biopsy methods suffer from a number of disadvantages. Because the probe must be physically moved about within the rectum by hand to identify and target the different areas of the prostate, it is difficult for physicians to precisely targeted biopsy sample locations, often causing the need for additional samples to be taken. Further, if a sample seems to confirm cancer, it is difficult for the physician to accurately know where in the prostate the sample was taken from, and so difficult to re-biopsy the same tissue location to confirm the cancer.

A number of systems or devices have been proposed for the purpose of better targeting biopsies. Batten, et al, (U.S. Pat. No. 5,398,690) discloses a slaved biopsy device, analysis apparatus, and process. In Batten, an ultrasound device is inserted into the male urinary tract through the penis, with the biopsy and treatment device inserted transrectally. Chin, et al, (U.S. Pat. No. 6,179,249) discloses an ultrasound guided therapeutic and diagnostic device. Chin is a flexible ultrasound device used for laproscopic surgery. Lin (U.S. Pat. No. 6,261,234) disclosed a method and apparatus for ultrasound imaging with biplane instrument guidance. Lin's ultrasound device uses two transducers to create two image planes, and has a biopsy needle guide which directs a biopsy needle at the intersection of the imaging planes. Burney, et al (U.S. Pat. No. 6,447,477) discloses surgical and pharmaceutical site access guide and methods. Burney shows a biopsy device in which a thick needle with side exit ports is inserted into the targeted tissue. Biopsy needles are then inserted into the thick needle, exiting out the side to take samples. Further, a number of systems have specified the use of flexible biopsy needle kits.

However, all of these inventions suffer from a number of disadvantages. All require specialized equipment, and do not make use of existing ultrasound systems and technology. All require the movement of the imaging device, making it more difficult to plan and target areas of the prostate for biopsy. Further, the flexible biopsy needles called out either require heating or additional force to cause them to fire, and are impractical for use with established prostate biopsy procedures and existing biopsy needle set firing devices.

Therefore, users would benefit from a biopsy system to allow a biopsy to be planned prior to the tissue sampling, to allow the biopsy needle to be precisely inserted into a targeted area and which is able to record the precise location from which the tissue sample is collected while the imaging device remains stationary. Users would also benefit from a flexible needle set which may be easily "fired" while in a curved position. Further, users would benefit from a means of precisely delivering a treatment to a targeted area of an organ or tissue mass.

SUMMARY OF THE INVENTION

It is the principal object of this invention to provide a device and method for precisely planning, undertaking and recording a multi-sample biopsy of a targeted tissue mass such as a prostate, improving physicians' ability to diagnose cancer.

Another object of the invention is to allow a biopsy plan to be formulated identifying the specific quadrants and areas of the prostate to be sampled.

Another object of the invention is to allow this biopsy plan to be saved as a reference point.

Another object of the invention is to allow a physician to adjust the biopsy needle guide to allow the physician to precisely insert the needle into the tissue at the planned location.

Another object of the invention is to allow a physician to monitor the needle set as it is inserted into the tissue, to verify that the needle is in the planned location.

Another object of the invention is to provide a biopsy needle guide which can be affixed to or associated with existing side-imaging transrectal ultrasound probes.

A further object of the invention is to allow the transrectal ultrasound probe to remain stationary while the biopsy samples are gathered from different areas of the prostate, thereby improving the accuracy of the procedure.

A further object of the invention is to allow the probe to remain stationary while the needle guide is moved longitudinally along the probe and is also rotated around the probe.

A further object of the invention is to provide a needle set guide which can redirect the needle set such that the needle set can be curved while still maintaining the freedom of movement to allow the firing and collecting of tissue samples.

A further object of the invention is to provide a biopsy needle set that may be redirected at an angle and further maintains its ability to be fired and so collect the tissue samples.

An object of an alternative embodiment of the invention is to allow a treatment plan to be formulated identifying the specific areas of tissue or an organ to be treated.

A further object of an alternative embodiment of the invention is to allow this treatment plan to be saved as a reference point.

Another object of an alternative embodiment of the invention is to allow a physician to precisely insert a needle or treatment delivery means into the tissue at the planned location.

Another object of the invention is to allow a physician to monitor the needle or treatment delivery method as it is inserted into the tissue, to verify that the needle or treatment delivery method is in the planned location.

These and other objects, advantages and features are accomplished according to the devices and methods of the following description of the preferred embodiment of the invention.

As noted the present invention relates to a biopsy targeting system for use with ultrasound imaging devices, and particularly for use in sampling prostate tissue. The biopsy targeting system consists of a redirecting biopsy needle guide which works in conjunction with a side-view or end-fire transrectal ultrasound probe, a cooperating software program which can be loaded and operated on a computer controlled ultrasound system, and a bendable needle set.

In use, the transrectal ultrasound probe is placed in the cradle of a stabilizer. The redirecting needle guide positioning assembly is also affixed to the cradle. The physician then advances and adjusts the cradle to allow the transrectal probe to be inserted into the rectum of a patient. The physician generates an ultrasound image while positioning the probe to insure that the patient's prostate is viewable within the viewing area of the probe. Once the probe is correctly positioned, the physician then locks the probe in place in the stabilizer.

With the transrectal probe in place, the physician initiates a full 3D scan of the prostate. The multiple image slices are captured by the ultrasound system. The physician then looks through these saved images, to identify possible problem areas of the prostate and further to decide which areas of the prostate to sample. Typically, physicians collect 9 to 18 tissue samples from different areas of the prostate. As part of this process, the physician is able to use the software program to project potential needle path lines onto the images of the prostate. These paths are shown as lines in views parallel to the needle path and as circles where the paths pierce the image plane. Each possible path is described by the positional settings of the redirecting needle guide. When the physician identifies a specific area to be sampled, the physician moves a projected needle path line to intersect the planed area to be biopsied. The physician continues to evaluate the prostate and target additional areas for sampling, again saving projected needle paths for each planned sample. Further, if the physician does not identify any possible problem areas, but wishes to take a standard biopsy, the physician can use a range of default setting on the computer program to project between 9 and 18 projected needle paths with a standard distribution throughout the prostate.

Once the biopsy is planned, the physician initiates the biopsy. All of the needle paths for a given longitudinal image are displayed on the ultrasound monitor. The display shows the coordinates of the planned needle paths which correlate to the positional setting of the redirecting needle guide. The physician then advances and/or rotates the redirecting needle guide to the correlating coordinates for the first planned needle path. The physician then inserts a flexible biopsy needle kit into the redirecting needle guide's needle insertion point. The needle set is advanced by hand through the needle set channel, including through the redirecting curve within the needle guide. This redirecting curve causes the needle to exit the needle guide, within the rectum of the patient, at an angle relative to the transrectal probe. The physician pushes the needle guide through the tissue of the rectal wall and into the prostate, monitoring the progress of the needle on the ultrasound system and insuring that the actual path of the needle matches the planned needle path being projected on the image. When the biopsy needle set has achieved the correct depth of penetration, the physician uses a standard biopsy firing gun to "fire" the needle set, causing the stylet and cannula to quickly extend in sequence, cutting and capturing a slice of prostate tissue in the specimen notch of the needle set. Because the specimen notch is substantially longer than in standard biopsy needles and the cannula body is flexible, the needle set is very flexible and able to be fired even though bent. The specimen notch is extended to the curved portion of the needle set within the redirecting needle set guide, allowing the stylet to be quickly moved in reference to the cannula without binding. With the needle still in the prostate, the physician saves the ultrasound image(s) on the computer program, creating a permanent record of the biopsy tissue location. The physician then removes the biopsy needle with captured tissue sample. Once removed, the cannula is retracted from the stylet, allowing the tissue sample to be placed into a tissue specimen dish. The physician then advances or moves the redirecting biopsy needle guide to the next planned needle path location, and repeats the procedure.

| Parts Numbers | |
|---|---|
| Rectum | 1 |
| Prostate | 2 |
| redirecting guide | 10 |
| alternative redirecting guide | 10A |
| positioning assembly | 11 |
| targeting software system | 12 |
| flexible needle set | 13 |
| cradle | 15 |
| stabilizer | 16 |
| ultrasound system | 17 |
| ultrasound system CPU side | 18 |
| view transrectal probe | 19 |
| monitor | 20 |
| probe tip | 22 |
| probe imaging window | 23 |
| guide body | 30 |
| needle set channel | 31 |
| needle set insertion point | 32 |
| needle set exit point | 33 |
| front body guide extensions | 34A, 34B |
| imaging cutout | 35 |
| needle set channel bend | 36 |

-continued

| Parts Numbers | |
|---|---|
| enlarged bend channel | 37 |
| insertable metal tube | 38 |
| rotational adjustment collar | 40 |
| fixed collar | 41 |
| longitudinal slides | 42 |
| longitudinal position controller | 43 |
| needle path location registry | 50 |
| needle path lines | 51 |
| needle path dots | 52 |
| flexible stylet | 60 |
| flexible cannula | 61 |
| tip | 62 |
| extended specimen notch | 63 |
| stylet body | 64 |
| cutting tip | 65 |
| cannula body | 66 |
| counter bore and taper | 67 |
| bending notches | 70 |
| tiered specimen notch | 71 |
| segmented specimen notch | 72 |
| removable needle set guide insert | 75 |
| stylet hub | 76 |
| cannula hub | 77 |
| strip | 78 |
| depth markings | 79 |
| cannula sheath | 81 |
| spiral cut | 82 |
| non-spiral cut portion | 83 |
| beveled edge | 84 |
| Biopsy attachment angle selector and display | 201 |
| Biopsy attachment depth selector and display | 202 |
| needle path coordinates display window | 204 |
| Finished with Biopsy Planning button | 206 |
| Remove selected biopsy location from plan button | 207 |
| Add selected biopsy location to plan button | 208 |
| Select pre-planned template | 209 |
| Sagittal image plane selector | 210 |
| Transverse image plane selector | 211 |
| Transverse image display | 212 |
| Sagittal Image display | 213 |

DESCRIPTION OF THE PREFERRED EMBODIMENT

Figure 1:
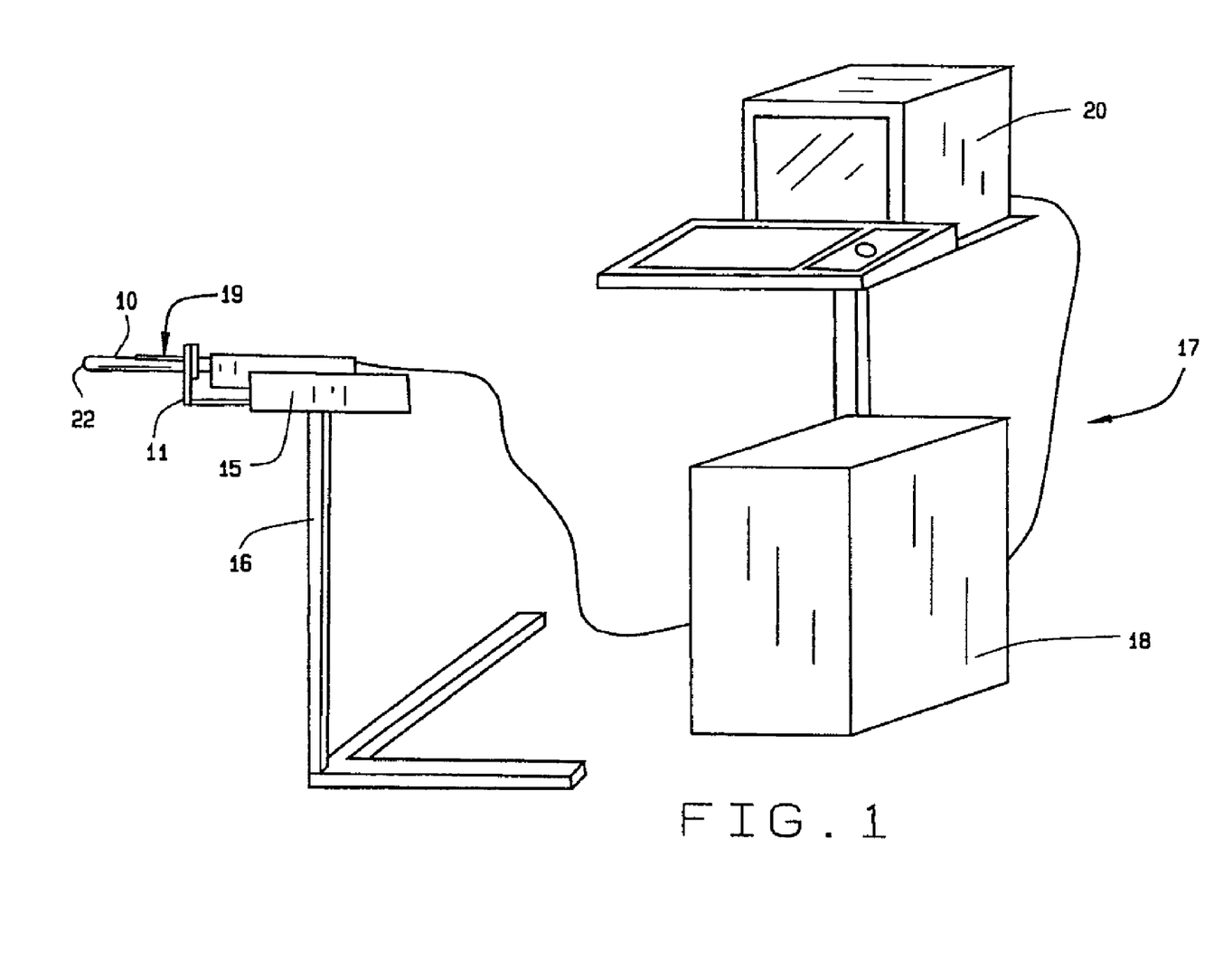
FIG. 1 is a perspective view of targetable biopsy system in conjunction with an ultrasound imaging system and stabilizer.
Figure 2:
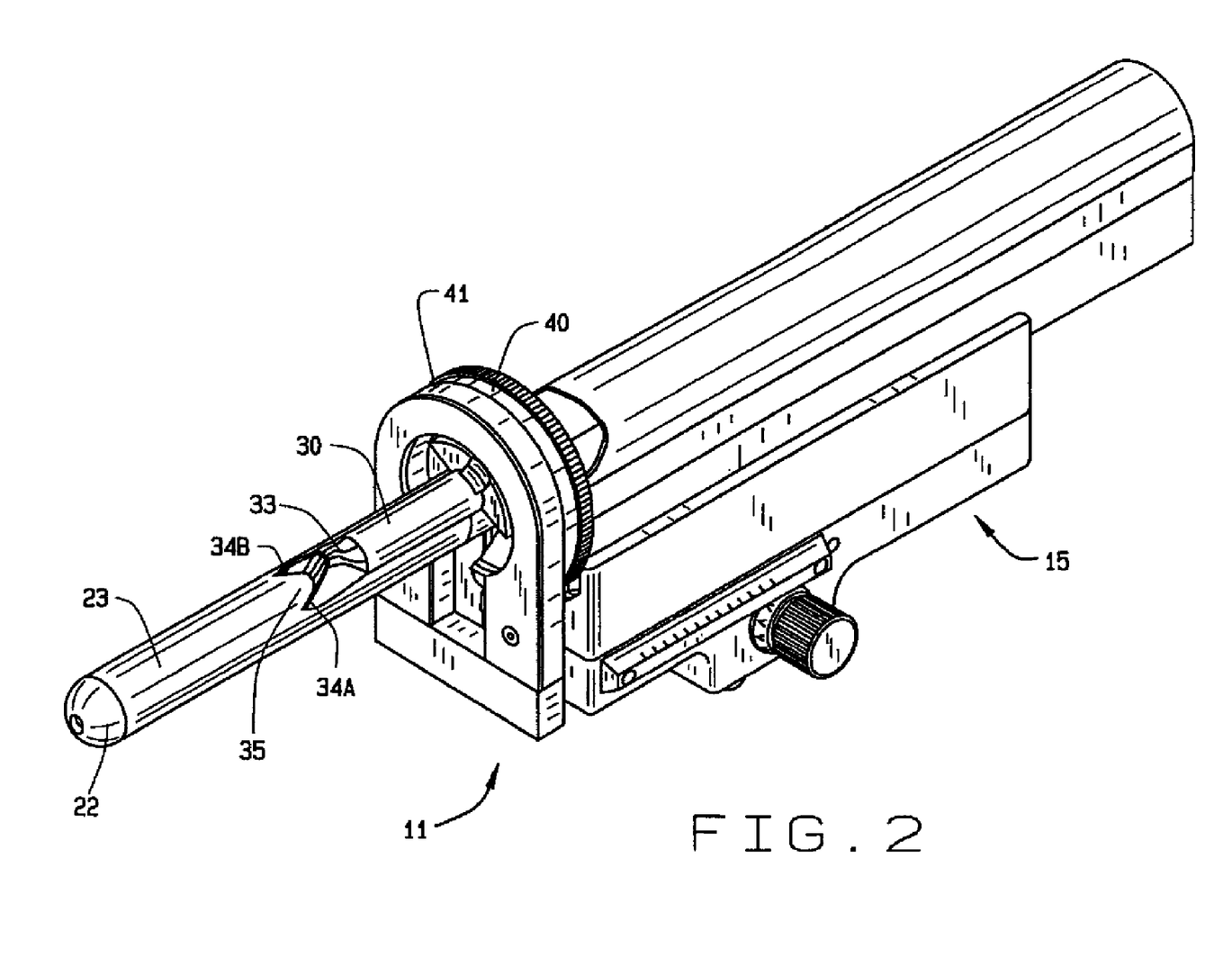
FIG. 2 is a perspective view of the redirecting needle set guide mounted on a side-imaging transrectal ultrasound probe.
Figure 7:
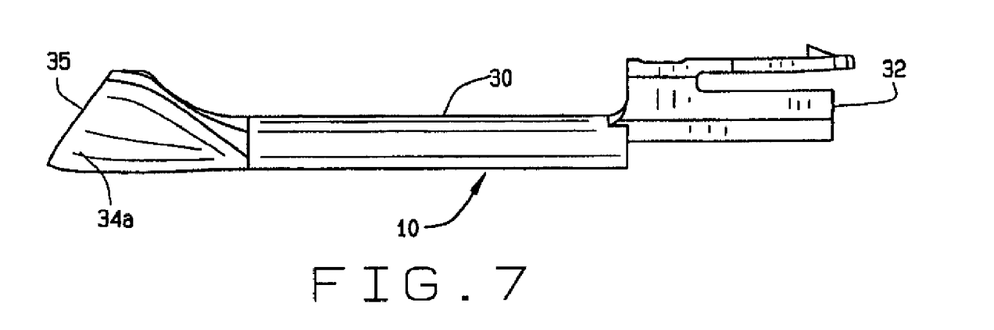
FIG. 7 is a side view of an embodiment of the targetable biopsy guide.
Figure 8:
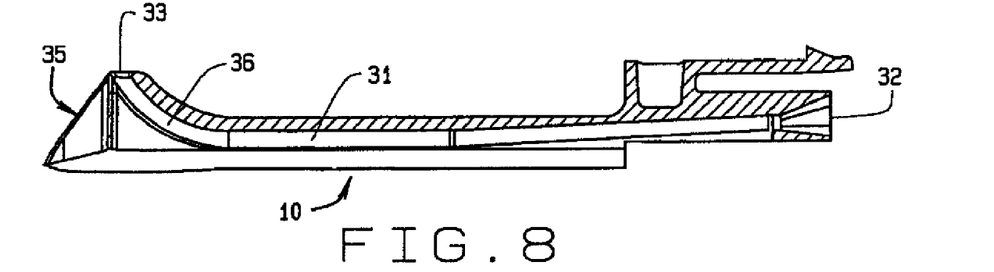
FIG. 8 is a side cutaway view of an embodiment of the targetable biopsy guide designed to be manufactured with an insertable metal tube.
Figure 9:
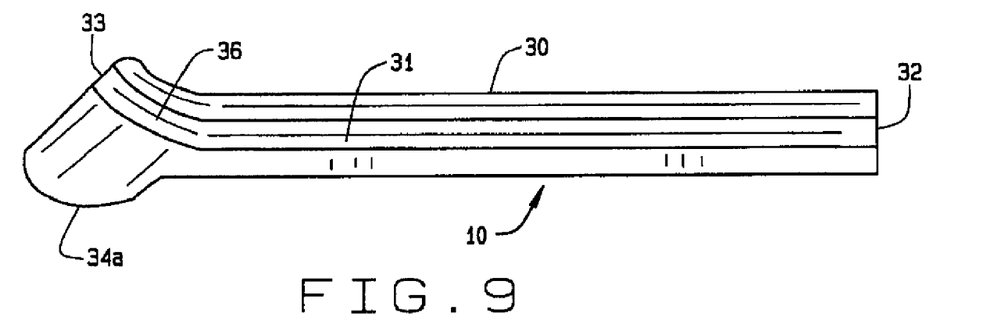
FIG. 9 is a side cutaway view of an alternative embodiment of the targetable biopsy guide.
Figure 10:
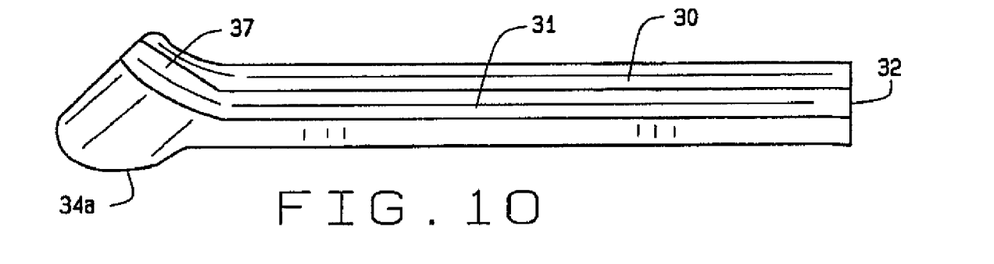
FIG. 10 is a side cutaway view of an alternative embodiment of the targetable biopsy guide with an enlarged bend channel.
Figures 20, 23:
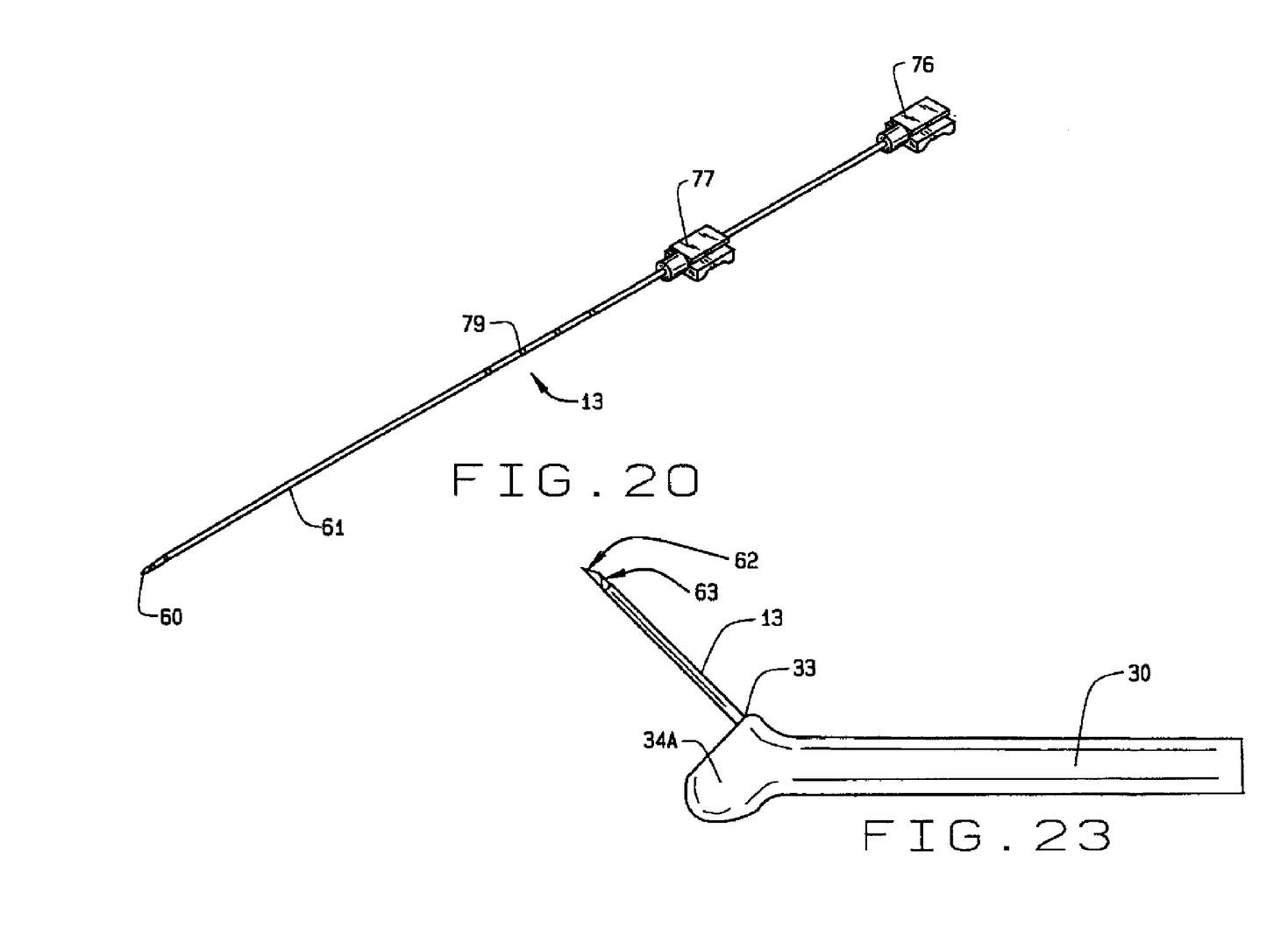
FIG. 20 shows a perspective view of an embodiment of the flexible needle set.
FIG. 23 is a side view of the redirecting guide with a flexible needle set inserted and extending out of the guide such that the needle set is bent by the needle set channel bend.

As seen in FIG. 1, the targeted biopsy system is comprised of a redirecting guide 10, positioning assembly 11, targeting software system 12 (loaded on CPU 18) and flexible needle set 13 (best seen in FIG. 20). The positioning assembly 11 is affixed to cradle 15, which is a part of stepper and stabilizer 16. Working in conjunction with the targeted biopsy system is ultrasound system 17, which is comprised of ultrasound system CPU 18, side view transrectal probe 19 and monitor 20. Side view transrectal probe is comprised of probe tip 22 and probe imaging window 23. As seen in FIGS. 2, 3A and 7, the redirecting guide 10 consists of guide body 30, needle set channel 31, needle set insertion point 32, and needle set exit point 33, front body guide extensions 34A and 34B, imaging cutout 35. As seen in FIG. 10, needle set channel 31 may be provided with enlarged bend channel 37. As seen in FIG. 8, the redirecting guide 10 may be provided with insertable metal tube 38. In an alternative embodiment, the redirecting guide may contain one or more pathways may be used for insertion of the biopsy needle kit. The redirecting guide may be comprised of a movable device such that the opening through which the needle kit exits may be moved relative to the opening into which the biopsy needle kit is placed. In a further alternative embodiment, the redirecting guide may straighten a previously curved biopsy needle kit such that the biopsy needle kit re-curve when leaving the redirecting guide.

Figure 3:
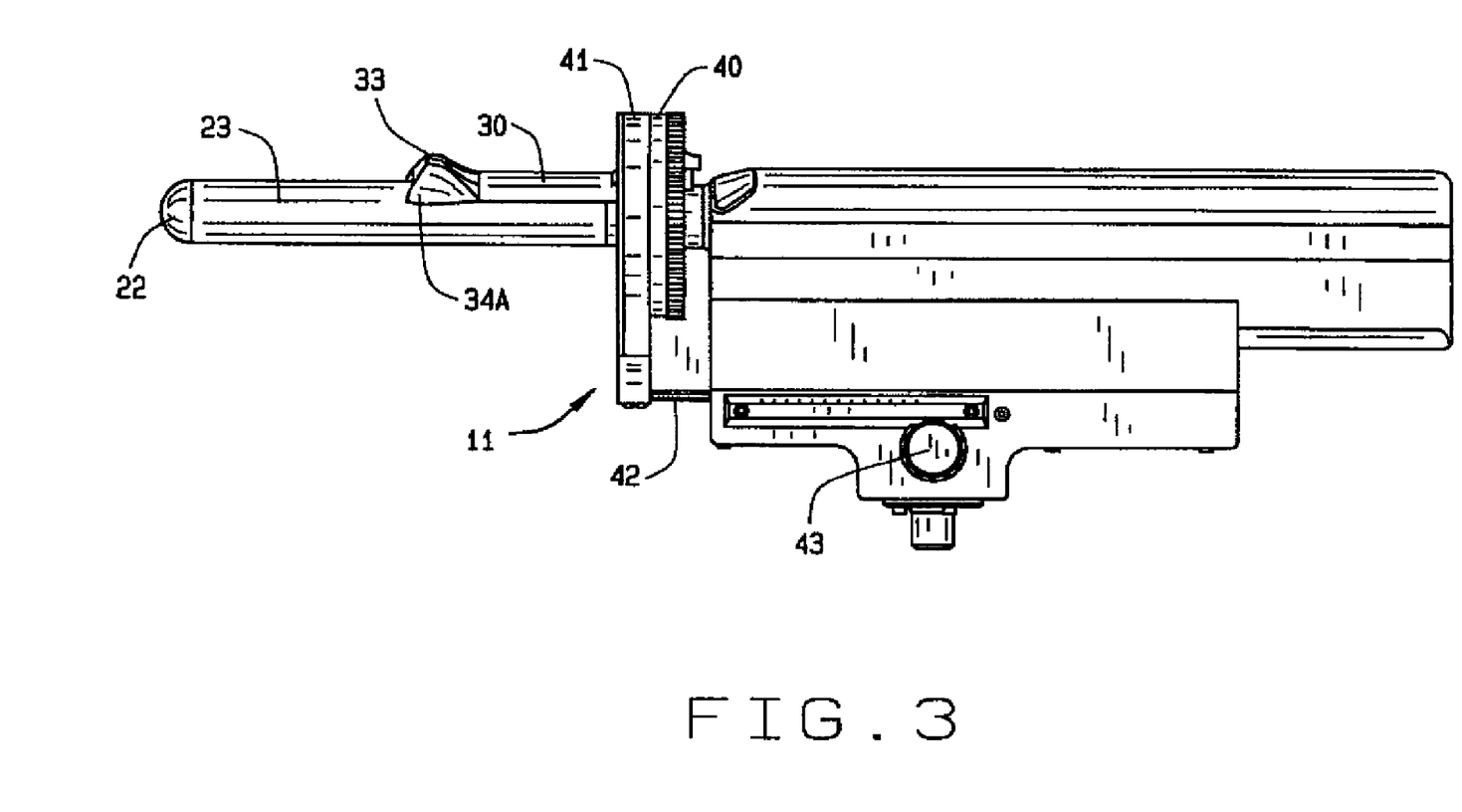
FIG. 3 is a side view of the redirecting needle set guide mounted on a side-imaging transrectal ultrasound probe, showing the guide positioning assembly.
Figure 3A:
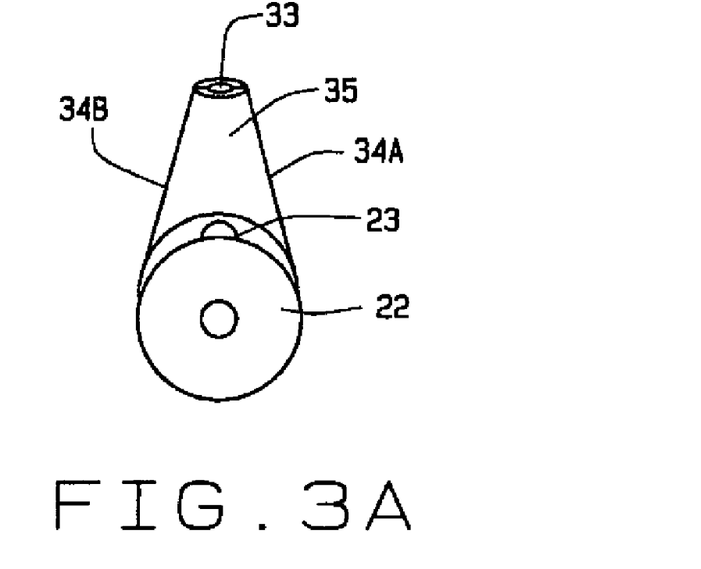
FIG. 3A is a front view of the redirecting needle set guide mounted on a side-imaging transrectal ultrasound probe in the manner shown in FIGS. 1, 2 and 3.

As best seen in FIG. 3, positioning assembly 11 is comprised of rotational adjustment collar 40, fixed collar 41, longitudinal slides 42 and longitudinal position controller 43.

Figure 4:
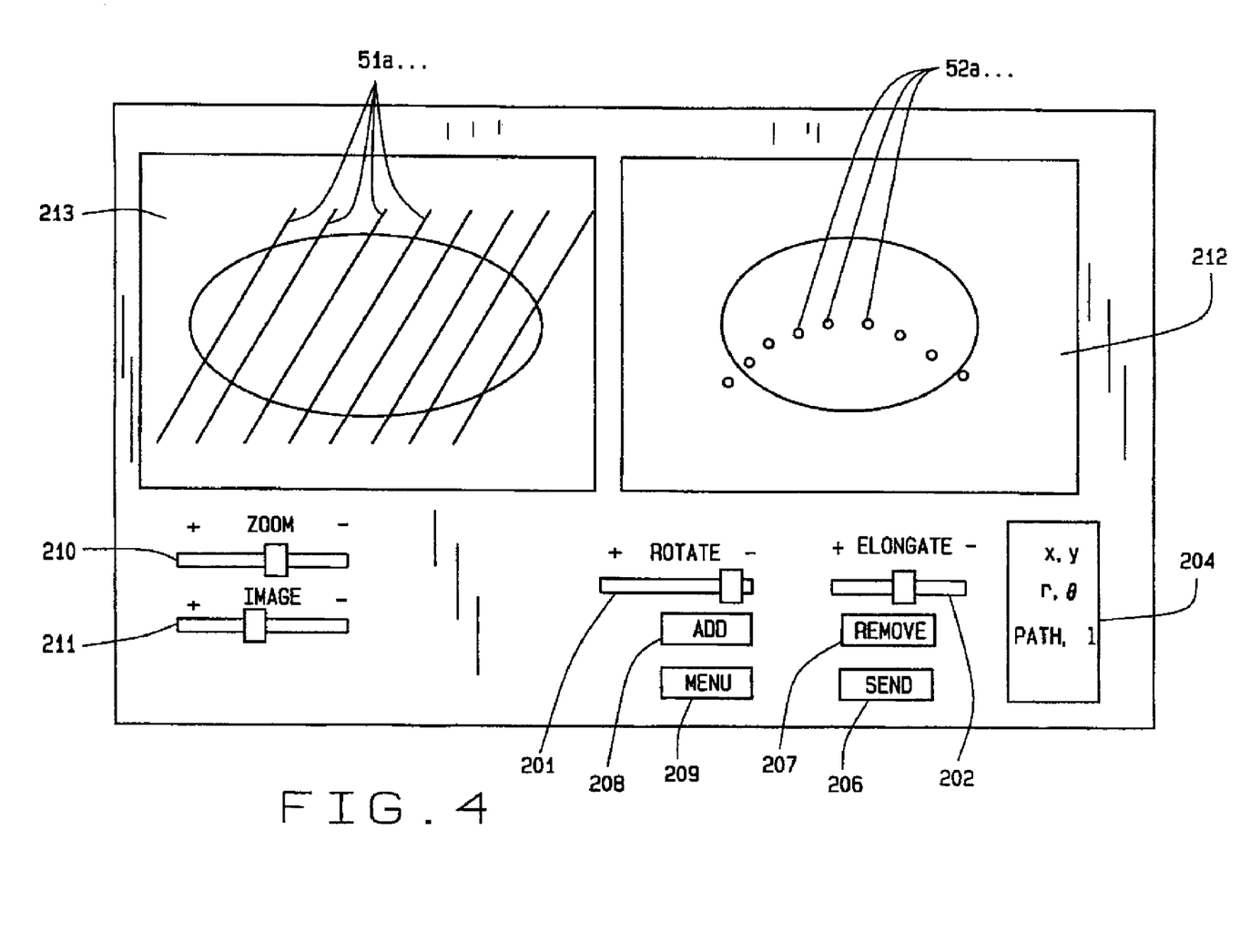
FIG. 4 is a planning software interface displayed on the monitor.

As best seen in FIG. 4, targeting software system 12 is comprised of transverse image display 212, Sagittal Image display 213, longitudinal projected needle path 51 and transverse projected needle path 52, in addition to various controls.

Figures 11, 12:
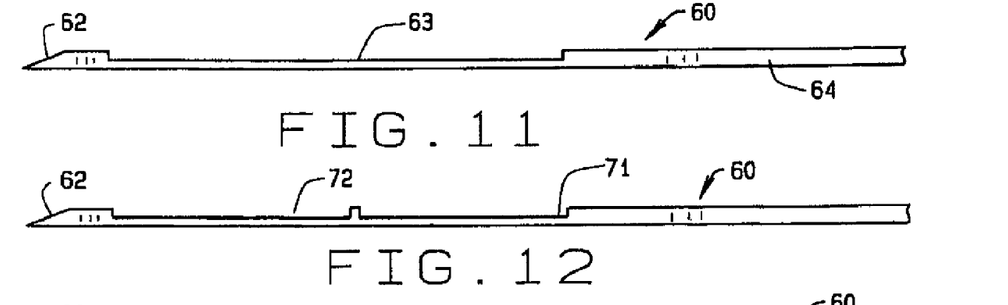
FIG. 11 shows a side view of a biopsy stylet with extended specimen notch.
FIG. 12 shows a side view of an alternative embodiment of the stylet with dual extended specimen notches.
Figure 13:
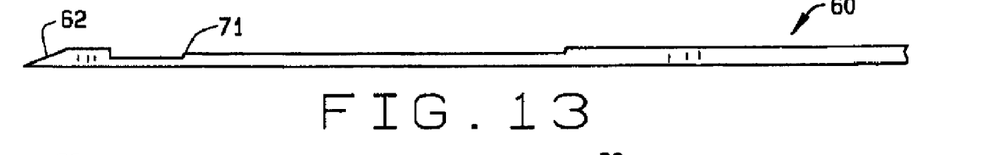
FIG. 13 shows a side view of an alternative embodiment of the stylet with a tiered specimen notch.
Figures 14, 15:
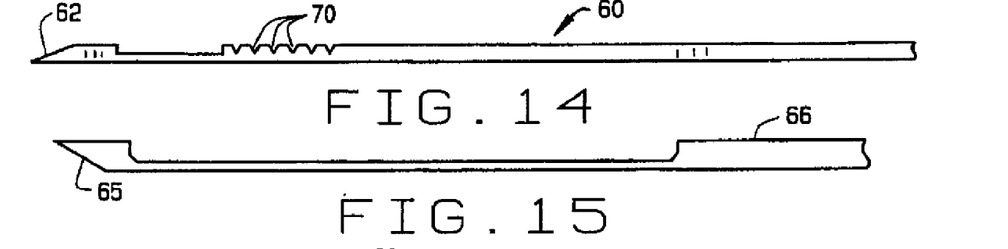
FIG. 14 shows a side view of an alternative embodiment of the stylet with multiple notches to facilitate bending.
FIG. 15 shows a side view of an embodiment of the cannula in which the cannula tube has been ground down along its length to leave a flexible spine.
Figure 14A:
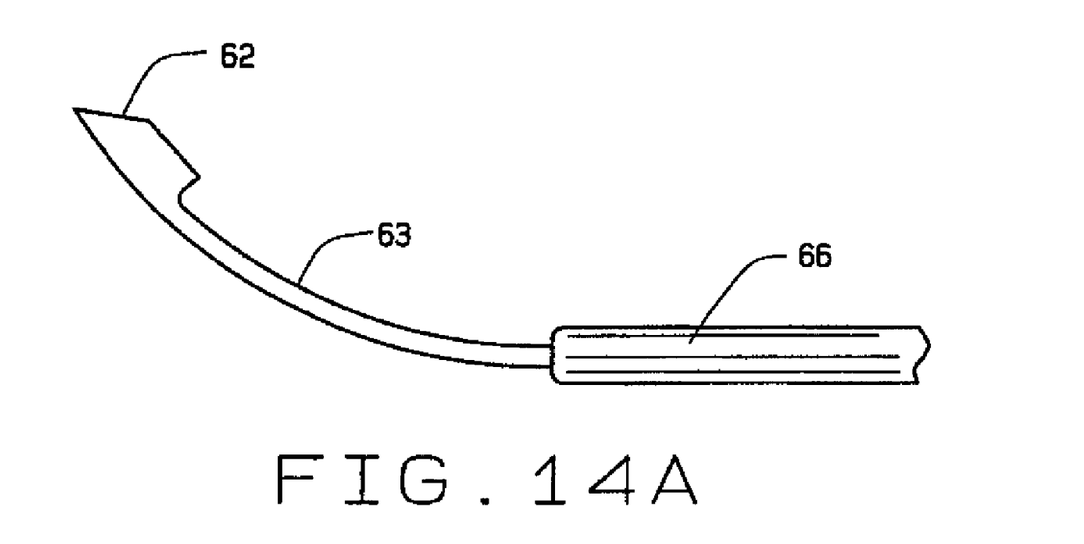
FIG. 14A is a side view of a flexible biopsy needle set in accordance with the present invention.

As best seen in FIG. 20, flexible needle set 13 consists of flexible stylet 60 and flexible cannula 61. Stylet 60 may be affixed to stylet hub 76, with cannula 61 affixed to cannula hub 77. Further, cannula 61 may be provided with depth markings 79. As seen in FIGS. 11 and 14A, the preferred flexible stylet 60 consists of tip 62, extended specimen notch 63 and stylet body 64 that is surrounded by the cannula body 66. As seen in FIG. 12, an alternative preferred flexible stylet 60 consists of tip 62 and segmented specimen notches 72a and 72b. Alternative embodiments of flexible stylet 60, as seen in FIGS. 13 and 14, contain bending notches 70 and tiered specimen notch 71.

Figure 16:
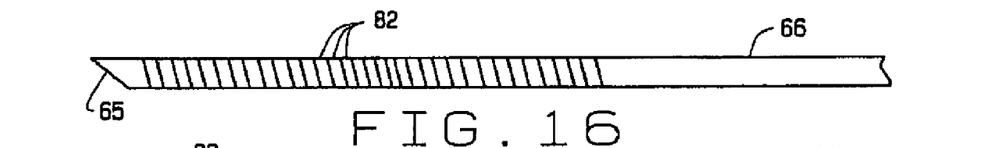
FIG. 16 shows a side view of an embodiment of the cannula in which the cannula tube has been spiral-cut along its length to facilitate bending of the cannula.
Figures 17, 18, 19:
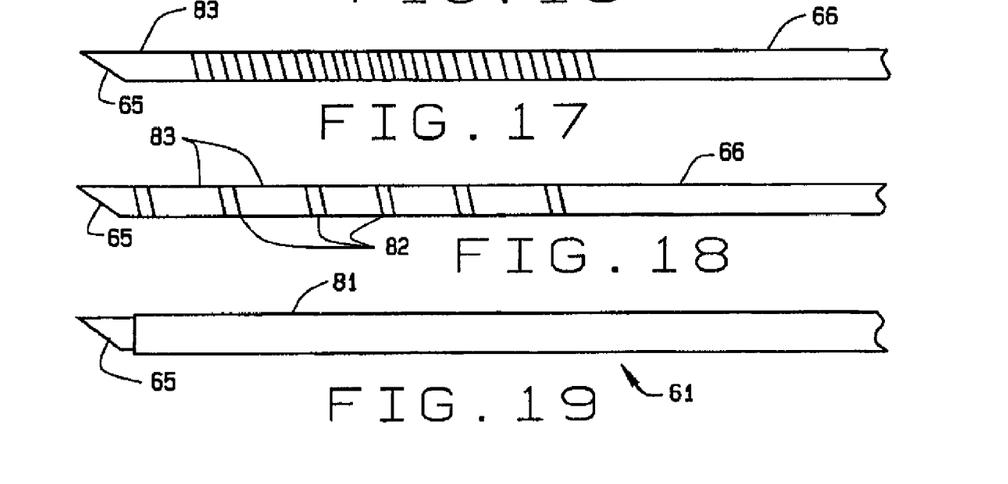
FIG. 17 shows a side view of an alternative embodiment of the cannula in which the tip of the cannula tube is uncut while the body of the cannula tube has been spiral-cut.
FIG. 18 shows a side view of an alternative embodiment of the cannula in which sections of the cannula tube alternate between cut and uncut.
FIG. 19 shows a side view of an embodiment of the cannula in which the cannula tube is encased in flexible tubing.

As seen in FIG. 19, the preferred embodiment of cannula 61 consists of cutting tip 65, cannula body 66 and cannula sheath 81. The cannula sheath may have beveled edges. As seen in FIG. 15, a portion of the body of flexible cannula 61 has been removed. As seen in FIG. 16, cannula body 66 may be provided with spiral cut 82 to facilitate bending. As seen in FIG. 17, in an alternative embodiment of cannula 61, cannula body 66 may be provided with non-spiral cut portion 83 at cutting tip 65, to facilitate the straight entry of the cannula into the tissue. As seen in FIG. 18, in a further alternative embodiment of cannula 61, cannula body 66 may be provided with non-spiral cut portions 83 interspersed with spiral cuts 82. In an alternative embodiment of flexible cannula 61 consists of a cutting tip inserted into the flexible cannula body.

It should be noted that both the stylet cannula can be made from a range of flexible materials, including combinations of one or more materials, to facilitate the bendability. This may include traditional materials used in medical devices, such as stainless steel, as well as materials such an Nitinol®. Furthermore, the cannula design may mirror the stylet, such that portion or portions of the metal cannula tube are removed to create a metal component which has a metal cutting tip, a long spine consisting of only a portion of the cannula wall in the flexible part of the cannula and then the full tubular cannula. Furthermore, the machine cannula may be partially or wholly incased in a cannula sheath, which may be plastic or some other material.

Figure 21:
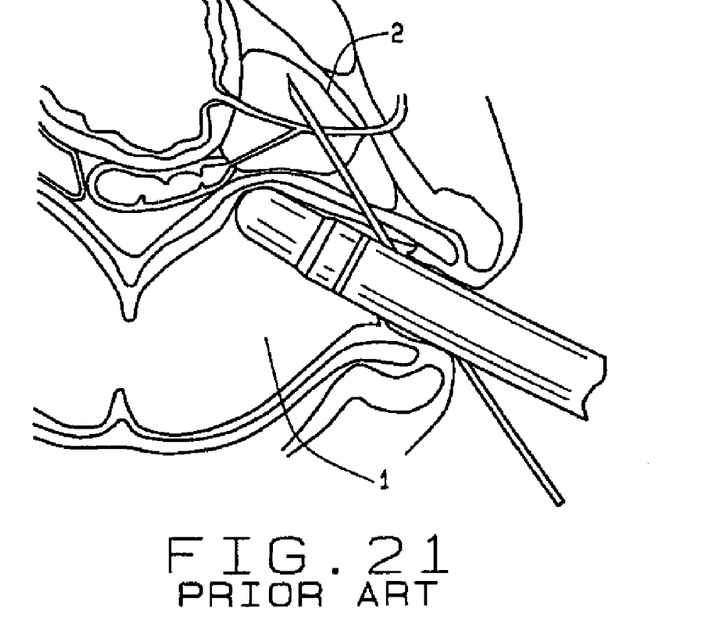
FIG. 21 is a side view of the traditional method of taking a prostate biopsy with a biopsy needle channel.

FIG. 21 shows a biopsy being performed using the standard method, using an end-fire ultrasound probe with a biopsy needle channel. The probe is inserted into the rectum, and then angled upward until the probe tip is pointed at the desired portion of the prostate. A needle set is then inserted through the biopsy needle channel guide into the prostate 2.

Figure 22:
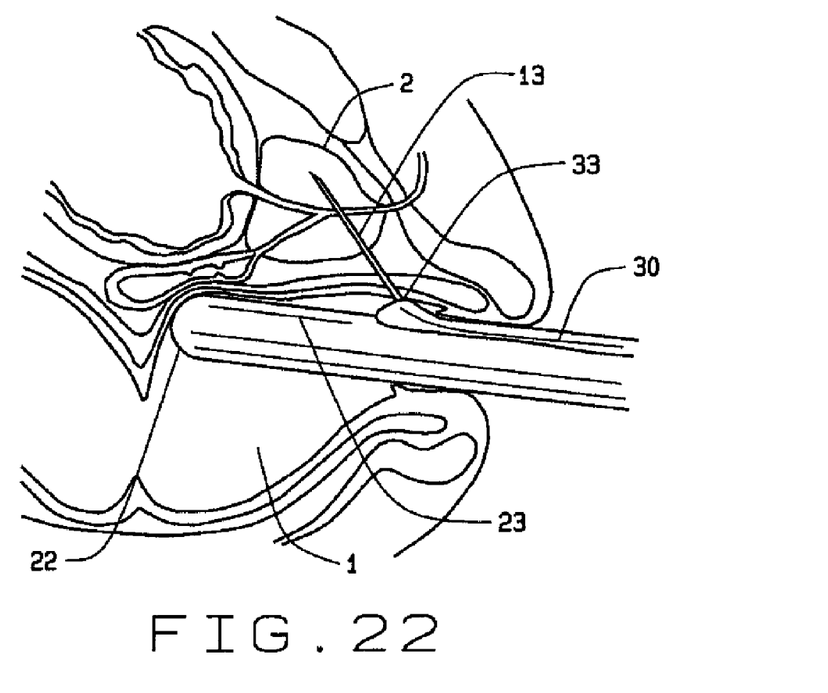
FIG. 22 is a side view of the bendable needle and biopsy targeting system mounted on a side-fired probe taking a biopsy.

In use of the preferred embodiment of the invention, as seen in FIGS. 1 and 22, side view transrectal probe 19 is mounted on the cradle 15 of a stabilizer 16. Redirecting guide 10 is also mounted on the cradle 15, such that guide body 30 sits atop probe tip 22. As seen in FIG. 2, front body extensions 34a and 34b partially wrap around probe tip 22 to help maintain the guide body 30 on the probe tip 22. The cradle 15 is moved forward, with the probe tip 22 inserted into patient's rectum 1. Probe tip 22 is generating ultrasound images, which are displayed on monitor 20. The physician uses this image to insure that the entirety of prostate 2 is viewable by probe imaging window 23. Once the probe tip 22 is correctly positioned, the physician locks in place cradle 15.

Figure 5:
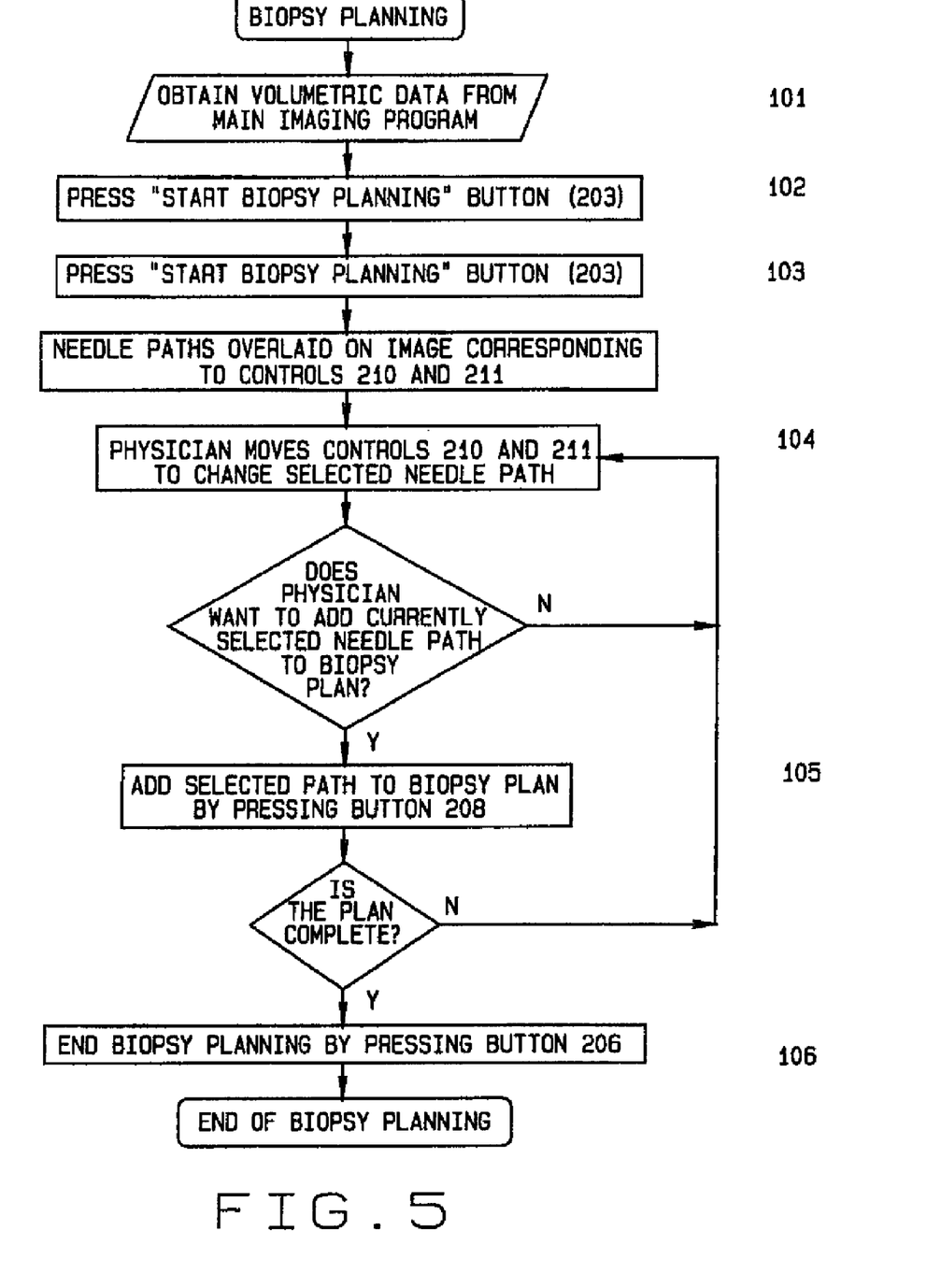
FIG. 5 is a schematic of the biopsy planning process.

The biopsy planning process is illustrated in FIG. 5. A representative display of the biopsy information to the user is shown in FIG. 4. The process begins with the planning software obtaining a set of volumetric data 101. The volumetric data consists of two sets of sampled images. One set is of longitudinal images sampled at a regular angular spacing, and the other is a set of transverse images sampled at regular depth spacing. If only one of the two sets is available, one may be interpolated from the other. The physician starts the planning process by pressing button 203 to satisfy step 102 of FIG. 4. For 103, the planning system overlays a series of lines 51a, b, c, etc. and dots 52 a, b, c, etc. on the images in panes 212 and 213. These lines and dots represent the available needle paths selectable with controls 40 and 43, and show where the needle intersects with image planes. Each line and dot combination is labeled with a coordinate 50 corresponding to a unique pair of setting for controls 40 and 43. The user can review the stored images using controls 210 and 211 to change the image viewed. For 104, the user can "simulate" the effect of controls 40 and 43 using on-screen controls 201 and 202 to adjust the selected needle path. The current path is displayed by changing the color of the appropriate line and dot (51 and 52, respectively). The user adds a specific needle path to the biopsy plan (105) by selecting button 208. Each time a path is selected, a record is placed into needle path coordinates display window 204 showing the coordinates of the path. The user may also remove a specific path from the plan by selecting button 207. When the plan is complete, the user clicks on the button 206 to send the planning process (106).

Figure 6:
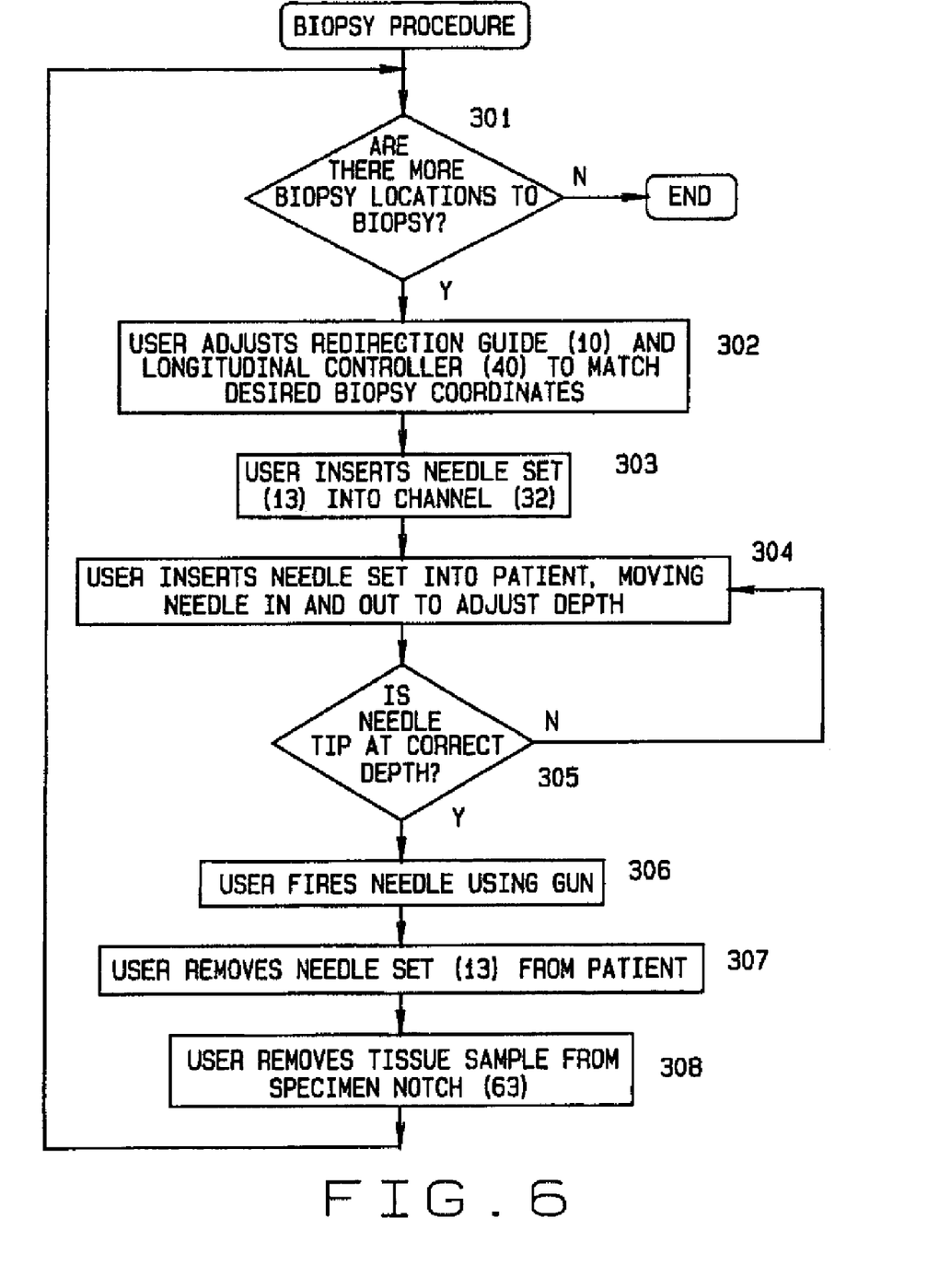
FIG. 6 is a schematic of the biopsy procedure.

Once the biopsy planning process has been completed, the physician or technician may then proceed with the biopsy procedure, to complete the series of precision located biopsy's to be taken through the usage of this instrument. For example, as can be noted in FIG. 6, once a biopsy procedure has been completed, the physician then determines whether any more biopsies are needed, and where the biopsy locations may be determined. This can be seen at 301. If no additional biopsies are required, this is the end of the procedure. If additional biopsies are considered as needed, the physician then adjusts the redirection of the guide 10, and the longitudinal controller 40, to mass the desired biopsy coordinates, as provided upon the scanner. This can be noted at 302. Then, the user inserts a needle set 13 into the channel 32, to prepare for additional biopsies. The physician then inserts the needle into the patient, moving the needle in and out to adjust for depth, as determined by the scanner, as can be seen at 304. Then, the physician can determine if the needle tip is at the correct depth, at 305. If it is not, then the physician may move the needle and adjust its depth further. If it is, the physician then fires the needle of the biopsy instrument, as at 306. Then the physician removes the needle set 13 from the patient, having taken the biopsy as required. Then, the tissue sample is removed from the biopsy needle notch, for further analysis by the lab. This can be noted at 308. When this is completed, this concludes the conduct of biopsies upon the patient.

As alternative to the procedure in FIG. 4, preplanned biopsy selection menu 209 allows the user to select a predetermined needle pattern, typically 9-12 needle paths, without having to select each needle path manually. The needle paths generated could need to be adjusted for the specific size of the organ. The size of the organ can be input by various means. The planning process allows the physician to modify the needle paths as needed and to approve that they are correct.

Projected needle paths 51a, 51b, etc, include needle path location registry 50, which indicate the horizontal and rotational position of the needle path in reference to the probe. Working from the saved biopsy plan, displayed in 204, the physician rotates redirecting guide 10 using rotational adjustment collar 40, and then advances the redirecting guide using longitudinal position controller 40, both of which have position information which correlates to the needle path location registry 50. As seen in FIG. 18, the physician inserts flexible needle set 13 into needle set insertion point 32 and into needle set channel 31. When the needle set 13 reaches needle set channel bend 36, the needle set 13 is redirected at an angle away from the axis of probe tip 22: Needle set 13 exits needle set exit point 33. Because of imaging cutout 35, the physician is able to see the needle set in the ultrasound image as it exits exit point 33, allowing the physician to insure that the needle set 13 is in the path marked by projected needle path 51a. The physician monitors the depth of the needle set 13 as it is pushed through the rectum wall and into the prostate 2. Once the desired depth is reached, the physician stops inserting the needle set 13. Using a standard biopsy gun, the needle set 13 is "fired". This causes flexible stylet 60 to rapidly advance a short distance, such that tissue from the prostate two prolapses into extended specimen notch 63. Almost instantaneously flexible cannula 61 quickly advances, also under spring loaded pressure or other motivational means, which serves to sever and capture the tissue that had prolapsed into the extended specimen notch 63. Because the extended specimen notch 63 extends to the point where flexible needle set 13 is bent in needle set channel bend, the stylet and cannula are able to fire without the two pieces binding together, allowing the specimen to be effectively captured. The physician then removes the flexible needle set 13 with the captured specimen. The specimen is removed from the flexible needle set, and the physician then resets the redirecting guide to the coordinates of the next saved projected needle path 51b. The process is repeated until the physician has captured all of the samples as planned using the targeting software system 12.

FIG. 23 provides a side cut-away view of the redirecting guide with a flexible needle set inserted and extending out of the guide such that the extended specimen notch is bent by the needle set channel bend.

In an alternative embodiment of the invention, the invention is used to plan and perform a targeted treatment of an organ or tissue mass. With the device in place, the process begins with the planning software obtaining a set of volumetric data. The planning system overlays a series of needle path lines and needle path dots on the images in panes 212 and 213, which represent the available needle paths with coordinates that match the coordinates on rotational adjustment collar 40 and longitudinal position controller 43 of positioning assembly 11. The user selects specific needle paths, which are saved the treatment plan. Preplanned treatment selections allow the user to select a predetermined needle pattern without having to select each needle path manually.

Working from the saved treatment plan, the physician rotates redirecting guide using rotational adjustment collar, and then advances the redirecting guide using longitudinal position controller, both of which have position information which correlates to the needle path location registry. The physician then inserts a flexible needle set or treatment delivery means into needle set insertion point 32 and into needle set channel 31. When the needle set or treatment delivery means reaches the needle set channel bend, the needle set or treatment delivery method is redirected at an angle away from the axis of probe tip 22. Needle set 13 exits needle set exit point 33. Because of imaging cutout 35, the physician is able to see the needle set or treatment delivery method in the ultrasound image as it exits exit point 33. The physician monitors the depth of the needle set or treatment delivery method as it is pushed into the targeted organ or tissue mass. Once the desired depth is reached, the physician is able to undertake the preferred activity. This may include using the delivery means to inject a solid, gas or liquid material or other treatment apparatus into the targeted organ or tissue mass. Further, the physician may insert an organism into the targeted organ or tissue mass. The material may be deposited and left in the targeted organ or tissue mass. Further, material previously deposited may be removed. The use of the deposited material may be as a treatment, a marker, or other uses. Further, the delivery means may be used to apply energy to a targeted organ or tissue mass, including but not limited to heat, cold, light and radiation. Once the treatment or marking is delivered, the physician then removes the flexible needle set or treatment delivery method, and then resets the redirecting guide to the coordinates of the next saved projected needle path. The physician has the option of saving the image of the treatment needle in the targeted organ or tissue mass, to record the location of the treatment as delivered. The process is repeated until the physician has treated or marked all of the targeted areas of the organ or tissue mass.

What is claimed is:

1. A system for targeted treatment comprising:
   a redirecting guide having a guide body and an elongate guide channel;
   an ultrasonic system having an ultrasonic system CPU, an ultrasonic probe and a display monitor that cooperate to generate and display ultrasonic images of a target tissue mass, wherein said ultrasonic probe comprises a probe tip adapted such that said guide body of said redirecting guide sits atop said probe tip and can be moved in different rotative positions and different longitudinal positions relative to said probe tip;
   an assembly for controlling rotational position and longitudinal position of said guide body of said redirecting guide relative to said probe tip;
   a targeting software system that displays ultrasonic images generated by the ultrasonic system in a transverse image display and a sagittal image display that are simultaneously displayed on said display monitor, wherein said wherein said transverse image display displays a transverse image sampled by said ultrasonic probe at a respective depth within said probe tip, wherein said sagittal image display displays a longitudinal image sampled at a respective angular orientation within said probe tip, wherein projections of a plurality of paths are simultaneously displayed on said transverse image display and said sagittal image display, each said path defined by a corresponding rotative position and longitudinal position of said guide body of said redirecting guide relative to said probe tip as controlled by said assembly; and
   a treatment delivering means which may be inserted into and through the elongate guide channel of said redirecting guide for treating a particular portion of the target tissue mass whose images are displayed on said monitor, wherein said particular portion of the target tissue mass corresponds to a given path defined by a corresponding rotative position and longitudinal position of said guide body of said redirecting guide relative to said probe tip as controlled by said assembly.

2. System according to claim 1, wherein:
   said given path is one of said plurality of paths projected onto said transverse image display and said saggital image display on said monitor.

3. System according to claim 1, wherein:
a respective path is shown as a line in the image plane of one of the transverse image display and the saggital image display.

4. System according to claim 1, wherein:
a respective path is shown as a graphical element in the image plane of one of the transverse image display and the saggital image display.

5. System according to claim 4, wherein:
the graphical element is depicted where the respective needle path pierces the image plane of the given image display.

6. System according to claim 4, wherein:
the graphical element comprises a circle.

7. System according to claim 1, wherein:
said treatment delivery means comprises a cannula.

8. System according to claim 1, wherein:
said treatment delivery means deposits a material in the particular portion of the target tissue mass.

9. System according to claim 8, wherein:
the material may be a solid, liquid or gas.

10. System according to claim 8, wherein:
the material is organic or a living organism.

11. System according to claim 8, wherein:
the material acts as a marker.

12. System according to claim 8, wherein:
the material provides treatment to the particular portion of the target tissue mass.

13. System according to claim 1, wherein:
said treatment delivery means deposits and removes a material in the particular portion of the target tissue mass.

14. System according to claim 13, wherein:
the material may be a solid, liquid or gas.

15. System according to claim 13, wherein:
the material is organic or a living organism.

16. System according to claim 13, wherein:
the material acts as a marker.

17. System according to claim 13, wherein:
the material provides treatment to the particular portion of the target tissue mass.

18. System according to claim 1, wherein:
said treatment delivery means removes a previously-deposited material in the particular portion of the target tissue mass.

19. System according to claim 18, wherein:
the material may be a solid, liquid or gas.

20. System according to claim 18, wherein:
the material is organic or a living organism.

21. System according to claim 18, wherein:
the material acts as a marker.

22. System according to claim 18, wherein:
the material provides treatment to the particular portion of the target tissue mass.

23. System according to claim 1, wherein:
said treatment delivery mean applies energy to the particular portion of the target tissue mass.

24. System according to claim 23, wherein:
the energy comprises light.

25. System according to claim 23, wherein:
the energy acts to apply heat or cold to the particular portion of the target tissue mass.

26. System according to claim 1, further comprising:
a path location registry which indicates horizontal and rotation position of a respective path in reference to the ultrasonic probe, wherein the assembly has position information which correlates to the path location registry.

27. System according to claim 1, wherein:
said redirecting guide comprises an entrance opening and exit opening adjacent opposed ends of the guide channel, the entrance opening receiving the treatment delivery means, the exit opening allowing for the treatment delivery means to exit therefrom, wherein the guide channel has a bend portion that redirects the treatment delivery means such that a portion of the treatment delivery means that exits from the exit opening of the redirected guide is angled away from the probe tip.

28. System according to claim 1, wherein:
said redirecting guide is selectively positioned or rotated relative to the probe consistent with a number of planned treatment locations.

29. System according to claim 1, wherein:
said redirecting guide is provided with demarcations or other indications of position relative to the probe tip.

30. System according to claim 1, wherein:
said transverse image display and said sagittal image display are simultaneously displayed in a side-by-side arrangement on said display monitor.

31. System according to claim 1, wherein:
said transverse image display and said sagittal image display are simultaneously displayed adjacent one another on said display monitor.

32. System according to claim 1, wherein:
said transverse image display and said sagittal image display are simultaneously displayed with interface means for initiating addition of a user-specified path to said plurality of paths.

33. System according to claim 1, wherein:
said transverse image display and said sagittal image display are simultaneously displayed with interface means for initiating removal of a user-specified path from said plurality of paths.

34. System according to claim 1, wherein:
said transverse image display and said sagittal image display are simultaneously displayed with interface means for initiating addition of a user-specified path to said plurality of paths.

* * * * *